United States Patent [19]

Pettit et al.

[11] Patent Number: 5,047,532

[45] Date of Patent: Sep. 10, 1991

[54] ISOLATION AND ELUCIDATION OF CEPHALOSTATINS 5 AND 6

[75] Inventors: George R. Pettit, Paradise Valley; Yoshiaki Kamano, Tempe, both of Ariz.

[73] Assignee: Arizona Board of Regents, acting on behalf of Arizona State University, Tempe, Ariz.

[21] Appl. No.: 386,427

[22] Filed: Jul. 28, 1989

[51] Int. Cl.$^5$ .................. C07D 491/22; A61K 31/495
[52] U.S. Cl. .................................... 544/230
[58] Field of Search ....................... 544/230

[56] References Cited

U.S. PATENT DOCUMENTS 4,873,245 10/1989 Pettit et al. ................. 544/230

OTHER PUBLICATIONS

Pettit et al., Chemical Abstracts, vol. 111, No. 229304, (1989), (Abstract for Can. J. Chem., (1989)).
Kamano et al., Chemical Abstracts, vol. 111, No. 4545, (1989), (Abstract for Tenne Yuki Kagobutsu Toronkai Koen Yoshishu, (1988)).

Primary Examiner—Mukund J. Shah
Assistant Examiner—E. Bernhardt
Attorney, Agent, or Firm—Richard R. Mybeck

[57] ABSTRACT

The Indian Ocean (South African) marine worm *Cephalodiscus gilchristi* (Hemichordata Phylum) has been found to contain a series of unusual disteroidal alkaloids designated the Cephalostatins which demonstrate exceptionally potent lymphocytic leukemia (murine P388) cell line inhibitory activity (to $ED_{50} 10^{-9}$ µg/ml). Two new disteriodal alkaloids bearing aromatic C-rings having $ED_{50}$ of $10^{-2}$ and $10^{-3}$ µg/mL were isolated and assigned structures based on rigorous interpretation of two-dimensional 400 MHz $^1$H and $^{13}$C-nmr. These substances were denominated Cephalostatin 5 and Cephalostatin 6, respectively.

3 Claims, No Drawings

ISOLATION AND ELUCIDATION OF CEPHALOSTATINS 5 AND 6

The work described herein was partially funded by the Arizona Disease Control Research Commision; under Contract N01-CM-97262 with the Division of Cancer Treatment, NCI, National Institute of Health (DHHS); PHS Grants CA-16049-05 and -11 awarded by the National Cancer Institute, DHHS.

INTRODUCTION

The present invention relates to the isolation and purification of new disteroidal alkaloids bearing aromatic C-rings, herein denominated Cephalostatin 5 and Cephalostatin 6, from marine sources and the discovery that both of these isolates are useful in that they each display significant cell growth inhibitory and antineoplastic activity against the P388 lymphocytic leukemia and other NCI test systems.

The general structure of the cephalostatins of the present invention is:

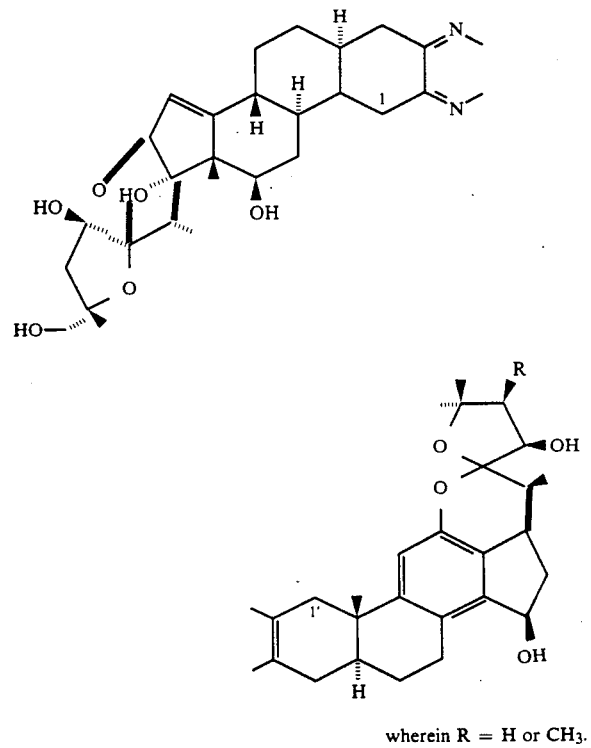

wherein R = H or CH$_3$.

BACKGROUND OF THE INVENTION

The invertebrate chordates have some vertebrate characteristics such as a dorsal tubular nervous system and notochord. Among such phyla lacking a vertebral column occurs the Hemichordata. The class Pterobranchia of this phylum has not previously been explored with respect to biologically active or other chemical constituents.

In late 1972, we collected by SCUBA (ca. 20 m) in the Indian Ocean off Southeast Africa, in areas patrolled by the great white shark *Carchorodon carchoris*, specimens from this class of the marine worm (~5 mm long in tube colonies) *Cephalodiscus gilchristi* (order Cephalodiscida). Two years later, methanol and water extracts of *C. gilchristi* demonstrated a confirmed active level against the U.S. National Cancer Institute's murine P388 lymphocytic leukemia (PS system) and obtained a 32-41% life extension of 25-37.5 mg/kg. Now after more than fifteen years of relentless research directed at discovering the active constituent(s) of *C. gilchristi*, we have succeeded in the isolation and structural elucidation of a series of powerful cell growth inhibitory substances with PS cell line ED$_{50}$ of $10^{-7}$ to $10^{-9}$ μg/ml. Our early work resulted in four substances which were denominated "Cephalostatin 1", "Cephalostatin 2", "Cephalostatin 3", and "Cephalostatin 4" and form the subject matter of our prior U.S. Pat. No. 4,873,245. Additional information including the taxonomy of the *Cephalodiscus gilchristie* is available from: E. J. W. Barrington, *The Biology of Hemi-chordata and Protochordata*, W. H. Freeman and Co., San Francisco, 1965; and Cilchrist, J. D. F., 1915, "Observations on the Cape Cephalodiscus (*C. gilchristi* Ridewood) and some of its early sates", *Ann. Mag. Nat. Hist.*, Ser. 8, 16, pp 233-246. Specimens of the *C. gilcristi* used by us were identified by the Museum National D'Histoire Naturelle, Paris, France in late 1977. Voucher specimens are on file at the Cancer Research Institute (CRI), Arizona State University, Tempe, Ariz. labelled M-1334 and GRP 8692. The specimens are available for inspection under the auspices of the Director of CRI.

The marine worm order Cephalodiscida (Hemichoradata phylum) contains two tube-living genera occurring primarily at considerable depths in the Southern hemisphere. Tubes containing colonies of these tiny marine animals are commonly found attached to marine life such as, bryozoans and sponges. Initial investigation of bioactive constituents in this worm class (Pterobranchia) by Pettit et al (J. Chem. Soc. Chem. Commun. 85 (1988) led to the discovery of a murine P388 lymphocytic leukemia (PS system) cell growth inhibitor denominated "Cephalostatin 1" in the South Africa (Indian Ocean) *Cephalodiscus gilchristi*. Subsequent isolation bioassays (PS) of *C. gilchristi* led to the isolation of two new and unusual disteroidal alkaloids bearing aromatic C-rings (shown above) which are herein designated "Cephalostatin 5" and "Cephalostatin 6." Both showed significant cell growth inhibition with P388 (PS ED$_{50}$ $10^{-3}$ and $10^{-2}$ μg/ml), respectively.

BRIEF SUMMARY OF THE INVENTION

Continued investigations of the marine worm order Cephalodiscida (Hemichordata phylum) led to the discovery of two new and unusual disteroidal alkaloids bearing aromatic C-rings herein denominated Cephalostatin 5 and Cephalostatin 6. Both Cephalostatin 5 and Cephalostatin 6 demonstrate significant cell growth inhibition (PS ED$_{50}$ $10^{-3}$ $10^{-2}$ μg/ml), respectively.

DESCRIPTION OF PREFERRED EMBODIMENTS

In one practice of the present invention, minor bioactive (PS leukemia) fractions prepared from a methylene chloride-methanol extract (from 166 kg of wet *C. gilchristi*) in accordance with the procedure described by Pettit et al, *J. Am. Chem. Soc.*, 1988, 110,2006, were separated by repeated gradient column chromatographic (partition on SEPHADEX LH-20, adsorption on silica gel, and HPLC) techniques. Final purification by HPLC using 30:70:0.1 hexane-ethyl acetate methanol afforded Cephalostatin 5 as a colorless solid (5.5 mg, 3.1×10⁻⁵% yield): m.p.>350° C.; [α]_{D+}100° (c=0.02, CH₃OH); SP-HRSIMS: (glycerol-CF₃SO₃H) 908.5164 (M+) for $C_{54}H_{72}N_2O_{10}$, calcd. 908.5187; and UV (CH₃OH): 290 (ε 9,500), 310 (sh) nm. Cephalostatin 6 was also isolated as a colorless solid (2.5 mg, 1.3×10⁻⁵% yield): m.p.>350° C.; [α]_{D+}100° (c=0.01, CH₃OH); SP-HRSIMS: (glycerol-CF₃SO₃H) 894.4985 (M+) for $C_{53}H_{70}N_2O_{10}$, calcd. 894.5031; and UV (CH₃OH): 289 (ε 10,000), 310 (sh) nm. The ¹H-abd ¹³C-nmr assignments are shown in Table 1 below. With the X-ray crystal structure assigned Cephalostatin 1 as a reference point, and the completely interpreted nmr spectra for prior Cephalostatins 1,2,3, and 4, it became possible using detailed analysis of high field two-dimensional nmr data and the mass spectra, to unequivocally assign the following structures to Cephalostatin 5 and 6, respectively.

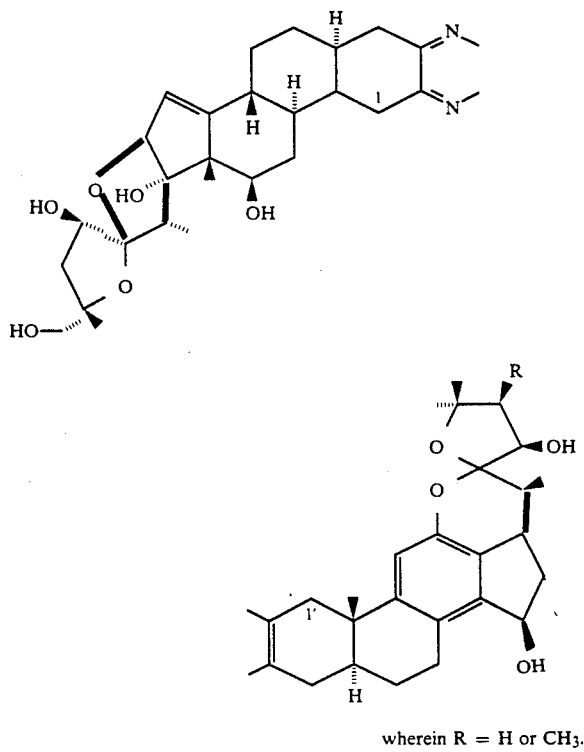

wherein: R=H or CH₃.

The ¹H- and ¹³C- nmr spectra of Cephalostatins 5 and 6 proved to be almost identical except for an additional methyl doublet at 1.07 ppm in the ¹H-nmr spectrum of Cephalostatin 6. By mass spectral analyses, each was found to possess one more degree of unsaturation than Cephalostatin 1, with Cephalostatin 6 bearing an additional methyl group. Their nmr spectra were found to be consistent with those found for Cephalostatin 1 through 4 with the exception that aromatic signals were uncovered in the ¹³C spectra. The nmr signals attributed to the "left-side" steroid unit in Cephalostatins 1-4 all appeared in the spectra of Cephalostatins 5 and 6 indicating that portion of the molecular skeleton remained unchanged. Subtraction of this unit from the spectra implied that the "right-side" steroid unit each contained nine degrees of unsaturations, present as three double bonds and six rings. Only three spin systems, A, B, and C, were found in the "right-side" steroid unit, as determined by COSY and homonuclear relayed COSY⁴ experiments. Spin system A was unambiguously assigned to C-4'-C-7'. The pressure of an nOe between the protons at 5.57 (H-15' in B) and 3.10 ppm (H-7a' in A) allowed assignment of spin system B to ring D and carbons 20' and 21' (cf. D). Location of the aromatic carbons in ring C was demonstrated by nOe effects between the aromatic proton at 6.92 ppm (C-11'; δ111.47) and one of the C-1' protons (3.54 ppm). The relatively high field chemical shift for the C-11' carbon indicated the presence of an oxygen atom at C-12', a structural feature consistent with all of the Cephalostatins so far isolated. System C was attributed to side-chain carbons 23' and 24'.

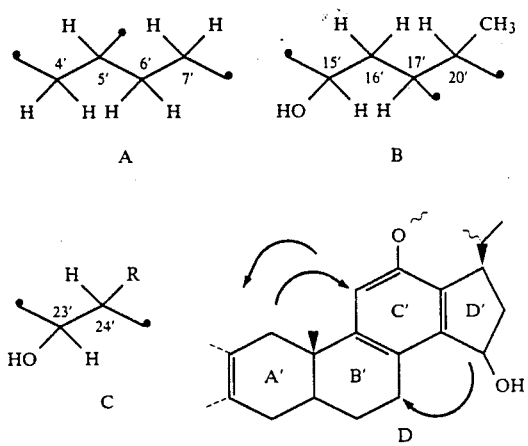

Next it remained to assign an acetal carbon (δ_c105.69), one oxygen atom, a gem dimethyl group, and fragment C, while forming two rings. Using results of a sensitivity enhanced heteronuclear multiple bond correlation experiment (HMBC⁵; see Table 1), and in keeping with the overall carbon skeleton deduced for Cephalostatins 1-4, the structures shown below were unambiguously assigned to Cephalostatin 5 and Cephalostatin 6 respectively. The stereochemistry at C15' was postulated to be R, assuming a biosynthetic relationship with Cephalostatin 4 which bears a βepoxy group at C-14'-15'. The other chiral centers were assumed to correspond essentially to their counterparts in Cephalostatin except for the stereochemistry at C-22' which remains undetermined.

While naturally occurring and synthetic steroids with ring-A aromatized are well known, steroids bearing an aromatic ring-C are quite rare and examples of such steriods having a biosynthetic origin are heretofore essentially unknown. The dramatic reduction in PS cell growth inhibition displayed by Cephalostatins 5 and 6 when compared to Cephalostatins 1-4 suggests that preservation of structural integrity in the "right-side" unit, including the C-D ring stereochemistry typical of, e.g., the steroid bufadienolides and cardenolides, is important to obtaining powerful inhibition of the PS leukemia. The atypical C-22' spiroketals involving C-18' in Cephalostatin 1 and C-12' in Cephalostatins 5 and 6, are also noteworthy.

GENERAL PROCEDURES

Chromatographic solvents were redistilled. SEPHADEX LH-20 and LH-60 (25-100 microns employed for gel permeation and partition chromatography) was obtained from Pharmacia Fine Chemicals AB, Uppsala, Sweden. Column chromatographic techniques utilizing silica gel (70-230 mesh) or silica gel 60 prepacked column was accomplished with material supplied by E. Merck (Darmstadt, West Germany). Both the PARTISIL M9 10/50 and PARTISIL M9 10/50 ODS-2 (C-18 reverse phase columns 9.4 mm i.d. × 500 mm) were used for hplc and obtained from Whatman, Inc., Clifton, New Jersey. Gilseon PC-220 racetrack and F-80 microfractionators connected to Gilson HM uv-visible Holochrome detectors were used for chromatographic fractionation experiments. Preparative layer plates were also obtained from Whatman, Inc., and the silica gel GF Uniplates for tlc were supplied by Analtech, Inc., Newark, Del. The tlc plates were viewed with uv light or developed with concentrated sulfuric acid, ceric sulfate-sulfuric acid or anisaldehyde acetic acid-sulfuric acid spray (heating at approximately 150° for 5-10 minutes).

The melting points are uncorrected and were observed with a Kofler-type melting point apparatus. Uv spectra were recorded using a Hewlett-Packard 8450 uv/vis spectrophotometer equipped with a HP 7225A plotter. Optical rotation values were obtained using a Perkin-Elmer 241 polarimeter. Infared spectral data was recorded with a Perkin-Elmer 299 IR spectrophotometer or a Nicolet MX-1 FT instrument. Mass specra were recorded with a Kratos MS-50 spectrometer. Nmr experiments were conducted with Bruker WH-90 and Bruker WH-400 instruments employing chloroform-d, or pyridine-$d_5$ as solvents and tetramethylsilane as an internal standard.

Animal Collection and Initial Experiments

The marine worm (~5 mm long in tube colonies) *Cephalodiscus gilchristi* (order Cephalodiscida) was collected by scuba (ca. −20 m) in the Indian Ocean off Southeast Africa. Thereafter methanol and water extracts of *C. gilchristi* reached the confirmed active level against the U.S. National Cancer Institute's murine P388 lymphocytic leukemia (PS system) with 32-41% life extension at 2-37.5 mg/kg.

A number of different approaches were tried to locate the cephalostatins with various recollections of *C. gilchristi*.

Animal Extraction and Solvent Partition Sequence

The marine worm (166 kg, wet weight) was extracted with methylene chloride-methanol at ambient temperature. The solvent was concentrated and the residue was partitioned between methylene chloride and water. The methylene chloride fraction was successfully partitioned using the system 9:1→4:1→3:2 methanol-water against hexane→carbon tetrachloride→methylene chloride, respectively. Both active methylene chloride and carbon tetrachloride fractions (28 g and 42 g respectively) were separated using a detailed bioassay (PS) guided series of chromatographic procedures as shown below in Separation Scheme 1, parts 1-3.

Separation of the 28 g active methylene chloride fraction was conducted as shown below in Separation Scheme 1, Part 1. The active fractions, G (0.19 g; $ED^{50}$ $8.2 \times 10_{-7}$) and H (0.21 g; $ED_{50}$ $2.6 \times 10^{-6}$ were combined. The total amount (0.42 g) of these combined fractions was then chromatographed on a column of silica gel using gradient elution with hexane-$CH_2Cl_2$—$CH_3OH$ (10:10:1→10:10:4) to give four active fractions designated as a, b, c and d in Scheme 1, part 2. Fraction C (0.17 g) was carefully separated by C-18 reversed phase hplc (PARTISIL-10, ODS-2) with $CH_3OH$—$H_2O$ (1:1 to $CH_3OH$) as mobile phase, followed by normal phase hplc [PARTISIL-10, silica gel]. Separation employing gradient elution with hexane-ethyl acetate-$CH_3OH$ (30:70:0) to 30:70:10) provided ten active fractions (denominated e to n, inclusive). Fraction g (10mg; $ED_{50}1.0 \times 10^{-4}$) was chromatographed on a column of SEPHADEX LH-20 (hexane-$CH_2Cl_2$—$CH_3OH$ 4:5:1) and the resulting PS cell line active material was further separated using C-18 reverse phase hplc (PARTISIL-10, ODS-2; 1:1 $CH_3OH$—$H_2O$ to $CH_3OH$). Final separation into fractions 0 and P was achieved by incorporating a gel permeation step in methanol using SEPHADEX LH-20. By this means two pure and PS cytostatic substances were isolated: Cephalostatin 5 (5.5 mg, $ED_{50}3.8 \times 10^{-3}$); mp 350° C.; $[\alpha]_{D+}100°$ (c=0.02, $CH_3OH$); SP-HRSIMS (glycerol-$CF_3SO_3H$) 908.5164 ($M^+$) for $C_{54}H_{72}$ $_2O_{10}$, calcd 908.5187; and uv ($CH_3$); 290 (9,500), 310 (sh) nm and Cephalostatin 6 a colorless solid (2.5 mg, $1.3 \times 10^{-5}\%$ yield); mp>350°; $[\alpha]_{D=}100°$ (c=0.01, $CH_3OH$); SP-HRSIMS: (glycerol-$CF_3SO_3H$) 894-4985 ($M^{30}$) for $C_{53}H_{70}N_2O_{10}$, calcd 894.5031; and uv ($CH_3OH$): 289 ($\epsilon$ 10,000), 310 (sh) nm. The $^1H$- and $^{13}C$-nmr assignments as shown in Table 1, below

TABLE 1

| NMR assigments and HMBC correlations for cephalostatin 6 (pyridine-$d_5$ sol.) | | | | | | | |
|---|---|---|---|---|---|---|---|
| left-side unit | | | | right-side unit (') | | | |
| $^{13}C$ | $^1H$ | mult, J (Hz) | HMBC (H to C#) | $^{13}C$ | $^1H$ | mult, J (Hz) | HMBC (H to C#) |
| C# | | | | | | | |
| 1  45.95 | 3.08 | d, 17.0 | 3, 5, 10, 19 | 47.24 | 3.56 | d, 16.9 | 3', 5', 10', 19' |
|  | 2.63 | d, 16.8 | | | 2.96 | | |
| 2  149.63 | | | | 149.54 | | | |
| 3  149.32 | | | | 148.94 | | | |
| 4  35.77 | 2.90 | | | 35.77 | 2.96 | | |
|  | 2.65 | d, 16.8 | | | 2.80 | | |
| 5  41.73 | 1.57 | | | 39.07 | 1.95 | m | |
| 6  28.19 | 1.49 | | | 25.29 | 1.71 | 2H | |
|  | 1.31 | | | | | | |
| 7  28.66 | 1.69 | | | 26.35 | 3.09 | br t, 2H | |
|  | 1.24 | | | | | | |
| 8  33.77 | 2.05 | | | 124.58 | | | |
| 9  53.20 | 0.87 | m | | 146.21 | | | |
| 10  36.27 | | | | 37.12 | | | |
| 11  30.00 | 2.05 | | | 111.46 | 6.93 | s | 8', 10', 12', 13' |
| 12  75.56 | 4.05 | ddd, 12.4, 4.9, 1.1 | | 149.55 | | | |
| 13  55.36 | | | | 127.88 | | | |
| 14  152.70 | | | | 144.30 | | | |
| 15  122.25 | 5.63 | s | 8, 13, 14, 16 | 74.54 | 5.55 | t, 5.5 | |
| 16  93.15 | 5.24 | s | | 39.83 | 2.38 | dd, 12.5, 6.0 | 13', 14', 15' |

TABLE 1-continued
NMR assigments and HMBC correlations for cephalostatin 6 (pyridine-d₅ sol.)
| | left-side unit | | | | right-side unit (') | | | |
|---|---|---|---|---|---|---|---|---|
| | $^{13}C$ | $^1H$ | mult, J (Hz) | HMBC (H to C#) | $^{13}C$ | $^1H$ | mult, J (Hz) | HMBC (H to C#) |
| 17 | 91.64 | | | | 36.90 | 2.18 | ddd, 12.5, 10.5, 5.5 | 13', 20', 21' |
| | | | | | | 4.44 | dt, 10.0, 6.0 | |
| 18 | 12.57 | 1.34 | s, 3H | 12, 13, 14, 17 | | | | |
| 19 | 11.69 | 0.71 | s, 3H | 1, 5, 9, 10 | 22.59 | 1.09 | s, 3H | 1', 5', 9' |
| 20 | 44.50 | 2.86 | | 13, 17, 21, 22, 23 | 37.00 | 2.27 | quint, 7.0 | 13', 21' |
| 21 | 8.99 | 1.35 | d, 7.1, 3H | 17, 20, 22 | 8.72 | 1.07 | d, 7.1, 3H | 17', 22' |
| 22 | 117.12 | | | | 107.35 | | | |
| 23 | 71.50 | 4.80 | | | 77.18 | 4.56 | q, 8.7 | |
| 24 | 39.51 | 2.73 | dd, 11.2, 8.0 | 22, 23, 26 | 46.22 | 2.58 | t, 11.2 | 23', 25', 26', 27' |
| | | 2.35 | t, 11.1 | 23, 25, 26, 27 | | 2.46 | dd, 11.7, 8.0 | 22', 23' |
| 25 | 82.80 | | | | 78.48 | | | |
| 26 | 69.27 | 3.81 | dd, 10.9, 5.3 | 25 | 30.12 | 1.27 | s, 3H | 24', 25', 27' |
| | | 3.71 | dd, 10.9, 4.6 | | | | | |
| 27 | 26.41 | 1.64 | s, 3H | 24, 25, 26 | 31.29 | 1.43 | s, 3H | 24', 25', 26' |
| OH's | | | | | | | | |
| —12 | | 4.70 | d, 1.1 | | | | | |
| —15 | | | | | | 6.54 | | |
| —17 | | 6.23 | s | 13, 17 | | | | |
| —23 | | 8.08 | d, 7.4 | | | 6.51 | | |
| —26 | | 6.55 | | | | | | |
*where no multiplicity is noted, it could not be determined because of overlapping signals.
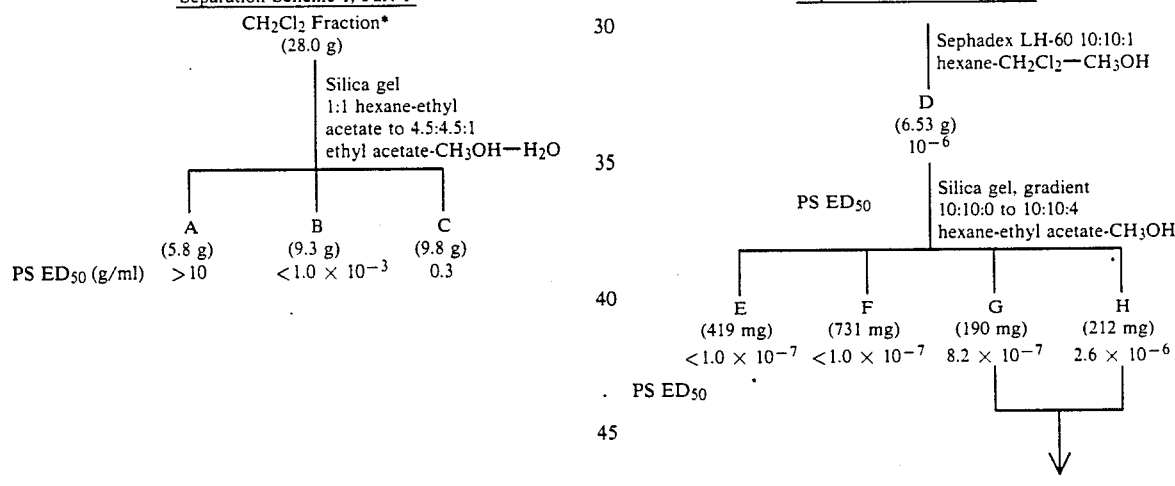
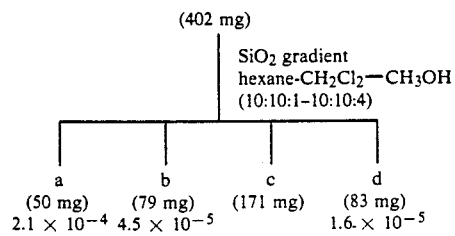

-continued

Separation Scheme 1, Part 2

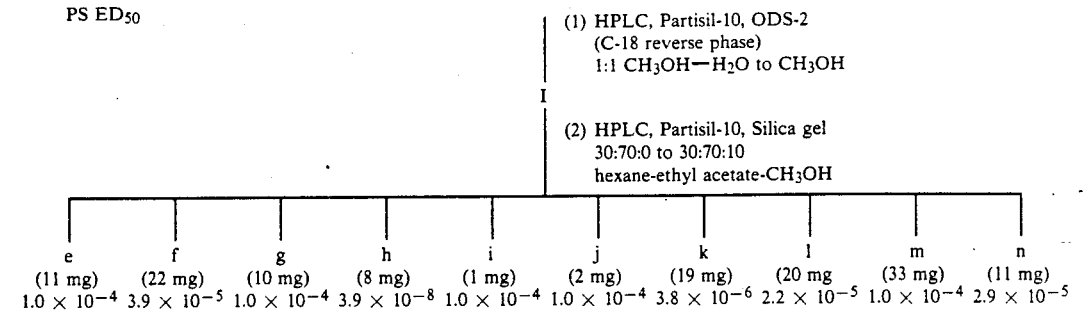

Separation Scheme 1, Part 3

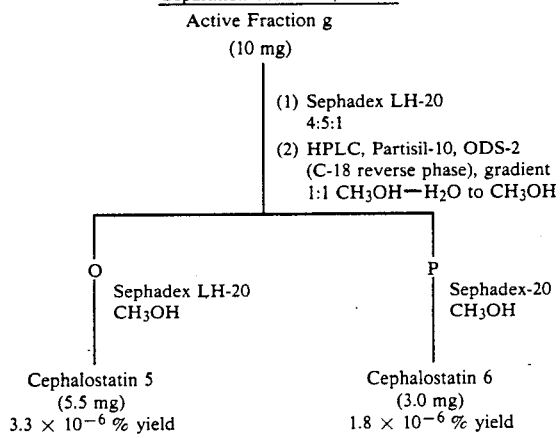

The administration of Cephalostatins 5 and 6 is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinomaa, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; intraperitoneal, 1 to about 500 mg/kg; subcutaneous, 1 to about 500 mg/kg; orally, 5 to about 1000 mg/kg;; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, broncholially, intravaginally, rectally, ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parental solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly communited diluent. The diluent can be an edible carbohydrate material such as lactose or starch. Advantageously a sweetening agent of sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium sterate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitaable comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets brokent into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carauba wax.

Fluid dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions, the water-soluble active ingredient can be dissolved in water for injection and filter sterilized before filling into a suitable vial or ampule and sealing. Advantageously, adjuvants such as a local anesthetic, preservative and buffering agents can be dissoved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid un it dosage form is prepared utilizing an active and a suitable pharmaceutiical vehicle, preferably P.F. water, a dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjets, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients can be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

To further aid in the understanding of the present invention, and not by way of limitation, the following examples are presented.

EXAMPLE 1

The marine worm *Cephalodicus gilchristi* was collected and 166 kg net weight was extracted with methylene chloride-methanol at ambient temperature. The solvent was concentrated and the residue partitioned between methylene chloride and water. The methylene chloride fraction was then partitioned further using the system 9:1→4:1→3:2 methanol-water against hexane→carbon tetrachloride →mthylene chloride, respectively. Both the carbon tetrachloride (42 g) and the methylene chloride (28 g) were collected for further use.

EXAMPLE 2

The active methylene chloride fraction from Example I was further separated using silica gel with 1:1 hexane-ethyl acetate to 4.5:4.5:1 ethyl acetate-$CH_3OH$—$H_2O$ into fractions A, B and C (as designated in Scheme 1, Part 1). Fraction B was segregated and further processed on SEPHADEX LH-60 with 10:10:1 hexane-$CH_2Cl_2$—$OH_3OH$ to isolate fraction D which was further separated on silica gel with a gradient of 10:10:0 to 10:10; 4 hexane—ethyl acetate—$CH_3OH$ to provide four separate fractions designated as E, F, G and H which were collected for further use.

EXAMPLE 3

Active fractions G and H from Example 2 were combined and then chromotagraphed on a column of silica gel using gradient elution with hexane-$CH_2Cl_2$—$CH_3OH$ (10:10:1→10:10:4) to give four distinct fractions designated as a, b, c and d in Scheme 1, part 2. Fraction C was carefully separated by C-18 reversed phase hplc using PARTISIL-10 as mobile phase followed by normal phase hplc (PARTISIL-10 silica gel).

EXAMPLE 4

Fraction C is separated employing gradient elution with hexane-ethyl acetate-$CH_3OH$ (30:70:02 to 30:70:10) to provide ten fractions (designated as e through n in Scheme 1, part 2).

EXAMPLE 5

Fraction g, obtained from Example 4, was hromotagraphed on a column of SEPHADEX LH-20 (hexane-$CH_2Cl_2$—$CH_3OH$ 4:5:1) and the resulting PS cell line active material was further separated using C-18 reverse phase hplc (PARTISIL-10, ODS-2; 1:1 $CH_3OH$—$H_2O$ to $CH_3OH$ to provide fractions O and P.

EXAMPLE 6

Fraction O from Example 5 was subjected to gel permeation in methanol using SEPHADEX LH-20 and concentrated to provide Cephalostatin 5.

EXAMPLE 7

Fraction P for Example 5 was subjected to gel permeation in methanol using SEPHADEX LH-20 to provide Cephalostatin 6 as a colorless solid.

EXAMPLE 8

Cephalostatin 5, obtained according to Example 6, was screened utilitzing NCI Protocol 1,200 (described in Cancer Chemotherapy Reports, part 3, Vol. 3, No. 2, September 1972, pages 9 et seq.) for lymphocytic leukemia P388 and provided ED$_{50}$ of $3.18 \times 10^{-5}$ μg/mL.

EXAMPLE 9

Cephalostatin 6, obtained according to Example 7 was solubilized and subjected to NCI Protocol 1200 to provide ED$_{50}$ of $10^{-2}$ μg/mL.

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. Compounds in substantially pure form denominated Cephalostatins having the structural formula:

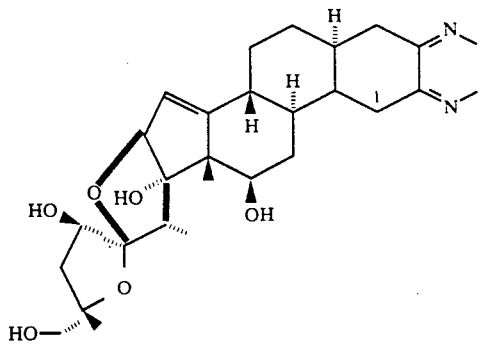

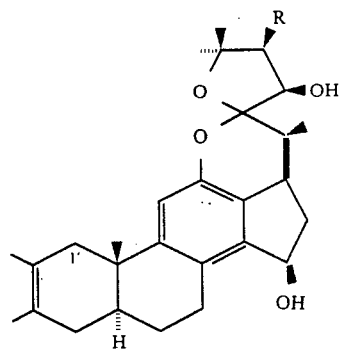

wherein R = H or CH$_3$.

wherein: R=—CH$_3$ or —H.

2. A compound according to claim 1 denominated Cephalostatin 5 in which R is —CH$_3$.

3. A compound according to claim 1 denominated Cephalostatin 6 in which R is H.

* * * * *